United States Patent [19]

Aneja

[11] Patent Number: 6,020,506
[45] Date of Patent: Feb. 1, 2000

[54] SYNTHESIS OF D-3 PHOSPHORYLATED PHOSPHOINOSITIDES AND ANALOGUES

[75] Inventor: Rajindra Aneja, Ithaca, N.Y.

[73] Assignee: Nutrimed Biotech, Ithaca, N.Y.

[21] Appl. No.: 08/862,865

[22] Filed: May 23, 1997

Related U.S. Application Data

[60] Provisional application No. 60/018,319, May 24, 1996.

[51] Int. Cl.[7] .............................. C07F 9/6561; C07F 9/10
[52] U.S. Cl. ............................................. 549/433; 558/160
[58] Field of Search ....................... 558/160, 87; 549/433

[56] References Cited

PUBLICATIONS

Database CAPLUS on STN® International, Chemical Abstracts Service, (Columbus, Ohio), Accession No. 1990:572539; Shashidhar et al. Chem. Phys. Lipids 53(1), 103–113 (1990), abstract, 1990.

Aneja et al. Tetrahedron Letters 38(5), 803–806 (Feb. 1997).

Aneja, et al., "1D– and 1L–1,2:4, 5–Di–O–cyclohexylidene–3–O–allyl–myo–inositols: Complementary Versatile New Starting Materials for Syntheses in the 1D–myo–Inositol Series," *Tetrahedron Letters*, vol. 37, No. 29, pp. 5081–5082, 1996.

*Primary Examiner*—Michael G. Ambrose
*Attorney, Agent, or Firm*—Williams, Morgan & Amerson

[57] ABSTRACT

Disclosed are unique starting materials, reaction sequences and intermediate compounds for the preparation of D-3-phosphorylated phosphoinositides (3-PPI) of unambiguous structure and absolute stereochemistry. The enantiomerically pure D-3-phosphorylated phosphoinositides also provided have many uses, including in the development of diagnostics and therapeutics based on the roles of 3-PPI in intracellular signaling.

15 Claims, 11 Drawing Sheets

RCO: Fattyacyl
PtdIns(3)P: $R^1 = R^2 = H$
PtdIns(3,4)P$_2$: $R^1 = P(O)(OH)_2$, $R^2 = H$
PtdIns(3,5)P$_2$: $R^1 = H$, $R^2 = P(O)(OH)_2$
PtdIns(3,4,5)P$_3$: $R^1 = R^2 = P(O)(OH)_2$

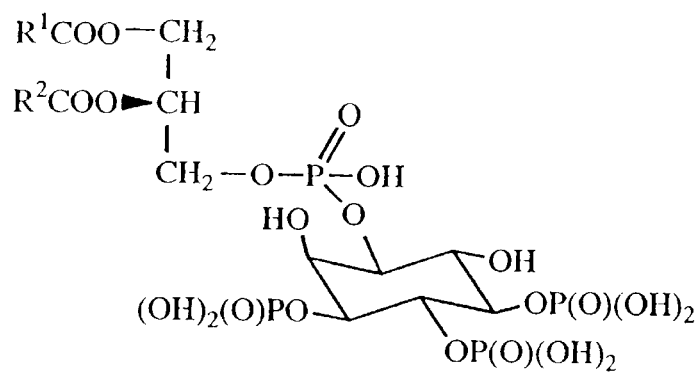
PtdIns(3,4,5)P₃
FIG. 2
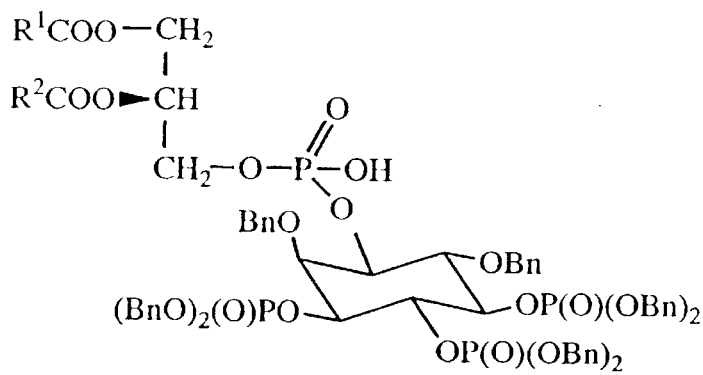
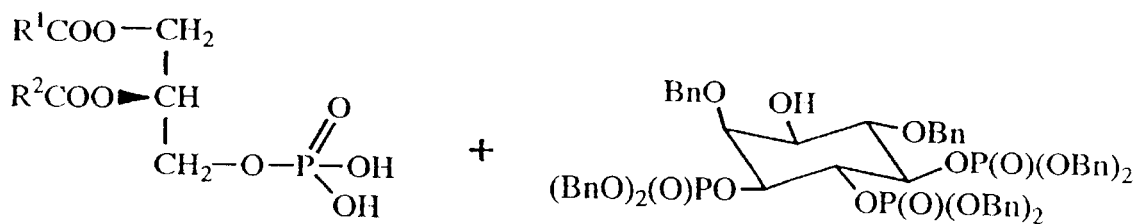
sn-3-Phosphatidic Acid    O-Protected 1D-myo-Inositol PtdIns(3,4,5)P₃

1a: R = H, DL series
1b: R = Camph.
  1: R = H, 1D series

1c: R = Camph.
1d: R = H, 1L series

PtdIns-benzyl ester 6,020,506

SYNTHESIS OF D-3 PHOSPHORYLATED PHOSPHOINOSITIDES AND ANALOGUES

The present application claims priority to provisional application Ser. No. 60/018,319, filed May 24, 1996.

This invention was partially made with funds provided by the Department of Health and Human Services under Grant No. NIH-GM49594. Accordingly, the United States Government has certain rights in this invention.

BACKGROUND OF THE INVENTION

The present invention concerns novel approaches for preparation by synthesis of the 3-phosphate derivatives of 1D-1-(1',2'-di-O-fattyacyl-sn-glycero-3'-phospho)-myo-inositols (PtdIns), referred to as the D-3-phosphorylated phosphoinositides or the 3-PPI (FIG. 1), their structural and stereochemical analogues, and, key starting materials and intermediates of these approaches.

3-PPI are relatively new members of the phosphoinositide group of cellular lipids with emerging critical roles in intracellular signalling. Synthetic 3-PPI and analogues are needed as reagents for defining their biological functions, and for developing diagnostics and therapeutics.

The 3-PPI (FIG. 1) including phosphatidylinositol-3-phosphate, PtdIns(3)P, and the bis- and tris-phosphate derivatives PtdIns(3,4)P$_2$ and PtdIns(3,4,5)P$_3$, have been found in eukaryotic cells (1), and the occurrence of PtdIns (3,5)P$_2$ has been suggested (2). These compounds have been demonstrated as activators of protein kinase C isoforms δ, ε, and " (3), and are putative messengers in cellular signal cascades pertinent to inflammation, cell proliferation, transformation, protein kinesis, and cytoskeletal assembly (4). Minute quantities are found in cells and biochemical studies to determine the cellular targets of the 3-PPI, their metabolic fate, and their roles in the cell cycle have been handicapped because 3-PPI have not been available. Methods for synthesis of 3-PPI have been sought recently (5). These prior art methods suffer from some unique and common problems related respectively to the choice of starting materials for the myo-inositol as well as the diacylglycero-lipid moieties in the 3-PPI. In contrast with the present invention, all start with sn-1,2-diacylglycerols as the lipid moiety in the 3-PPI, and consequently are prone to problems of poor chemical stability endemic to 1,2-diacylglycerols. The latter isomerize readily via neighboring O-acyl migration to equilibrium mixtures comprising the 1,2-, 1,3- and 2,3-diacylglycerols (6). This equilibration is tantamount to racemization which is virtually complete for sn-1,2-di(short-chain)fattyacylglycerols. Therefore, resulting 3-PPI may contain racemic 1,2-2,3- and 1,3-difattyacyl structures, especially with hexanoyl and related short-chain fattyacyls.

SUMMARY OF THE INVENTION

Accordingly, it is a principal object of the present invention to provide novel general approaches to synthesis, including novel starting materials, reaction sequences, and novel intermediate compounds, for preparation of the 3-PPI and structural analogues, all of unambiguous structure and absolute stereochemistry in the myo-inositol as well as the sn-glycerol moieties. The present starting materials, reaction sequences, and intermediate compounds, individually and collectively, have utility as materials and processes for obtaining the 3-PPI. The 3-PPI and analogues, in turn, have utility not only as research reagents but also for the development of diagnostics and therapeutics based on the roles of 3-PPI in intracellular signalling. In similar investigations of the biological roles of other bioactive compounds, analogues with reporter groups such as fluorescent tags, are often useful, and so intermediates of 3-PPIs conjugatable to reporter groups are sought.

Broadly, the invention embodies two complementary strategic approaches, and the starting materials and intermediates involved in each, based respectively on (i) synthesis from novel enantiomerically pure myo-inositol derivatives and phosphatidic acids, and (ii) partial synthesis by regioselective 3-phosphorylation of preformed phosphatidylinositol or derived phosphates.

According to one embodiment of the invention, synthesis is carried out by a novel unified approach which is suitable for facile synthesis of all cellular PtdIns-3-phosphates. It is based on the retrosynthetic analysis shown for PtdIns(3,4, 5)P$_3$ as an example in FIG. 2. The approach has several novel features. One, it uses 1D-1,2:4,5-di-O-cyclohexylidene-3-O-allyl-myo-inositol (—)-1 as purposely designed starting material and 1D-1,2-O-cyclohexylidene-3-O-allyl-6-O-benzyl-myo-inositol (+)-3 as a key myo-inositol synthon. Two, it incorporates strategic O-protection by and sequentially invariant removal of allyl, 4-methoxybenzyl, and benzyl protecting groups from the inositol hydroxyls destined to appear in the target structures as phosphate, phosphatidyl, and free hydroxyl respectively. Three, it employs preformed 1,2-di-O-fattyacyl-sn-glycero-3-phosphoric acid (sn-3-phosphatidic acid) as the lipid synthon for coupling to appropriately O-protected myo-inositol by a phosphodiester condensation. The sn-3-phosphatidic acid are relatively stable compounds with well established absolute stereochemistry, and their application in the present invention avoids the problems of structural and stereochemical isomerization associated with the application of sn-1,2-fattyacylglycerol in the prior art. As a consequence, the approach uniquely provides unambiguous structural and stereochemical control in the myo-inositol as well as the sn-glycerol moieties, and is applicable for both short-and long-chain fattyacyl types (7). Compared with the long-chain types, the short-chain phosphoinositides are considered to be more useful in biochemical investigations (3, 4). The phosphodiester condensation products are substrates for lipolytic enzyme phospholipase A$_2$ and thus are valuable for incorporating additional useful structural features at a relatively late stage in synthesis. For instance, after lipolysis followed by esterification to introduce (ω-amino-fattyacyls at the sn-glycerol-2 position, the ω-amino group may be conjugated to fluorescent and related reporter groups. The aforementioned attributes are useful and these distinguish the present invention from related literature methods cited above (5).

According to another embodiment of the invention, partial synthesis is based on the retrosynthetic analysis illustrated for PtdIns(3,4,5)P$_3$ from PtdIns(4,5)P$_2$ in FIG. 3. It comprises the regioselective 3-phosphorylation of preformed phosphatidylinositol or derived phosphates but lacking the D-3-phosphate, for the synthesis of the 3-PPI. The preformed PtdIns obtained from natural plant or animal cell sources contain (poly)unsaturated fattyacyls. Using such natural or the corresponding synthetic phosphatidylinositols with unsaturated fattyacyls as the starting materials for 3-phosphorylation as disclosed in the present invention provides methods for the synthesis of 3-PPI containing (poly)unsaturated fattyacyls. These 3-PPI have special physical properties such as lower chain melting transitions for the fattyacyls than for the corresponding saturated fattyacyls, and special bioactivity related to the number, location, and stereochemistry of the double bonds in the fattyacyl chain, and so are desirable. These 3-PPI cannot be prepared by the literature methods (5).

BRIEF DESCRIPTION OF THE DRAWINGS

FIG. 2 illustrates retrosynthetic analysis of the D-3-phosphorylated phosphoinositide PtdIns(3,4,5)P$_3$ for synthesis from sn-3-phosphatidic acid and a selectively substituted myo-inositol.

DETAILED DESCRIPTION OF THE INVENTION

Synthesis from myo-Inositol

Figure 1:
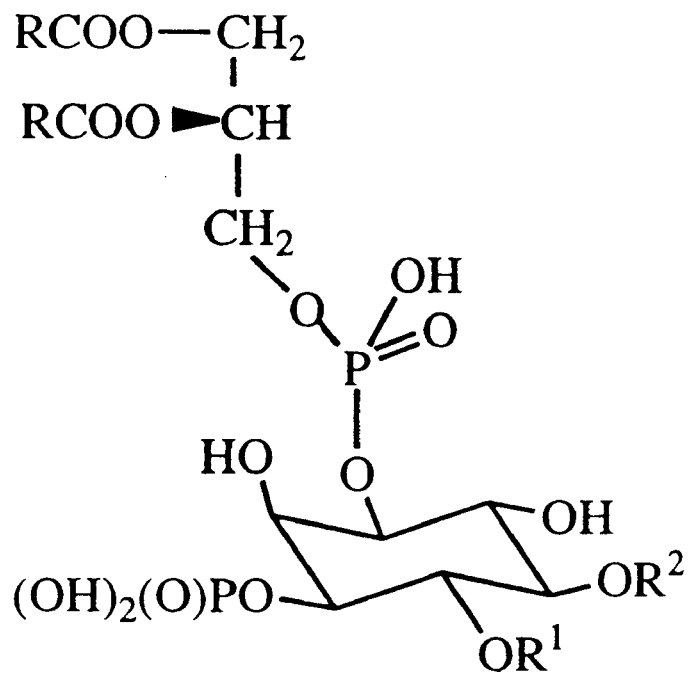
FIG. 1 illustrates the structure and stereochemistry of the D-3-phosphorylated phosphoinositides (the 3-PPI).
Figure 3:
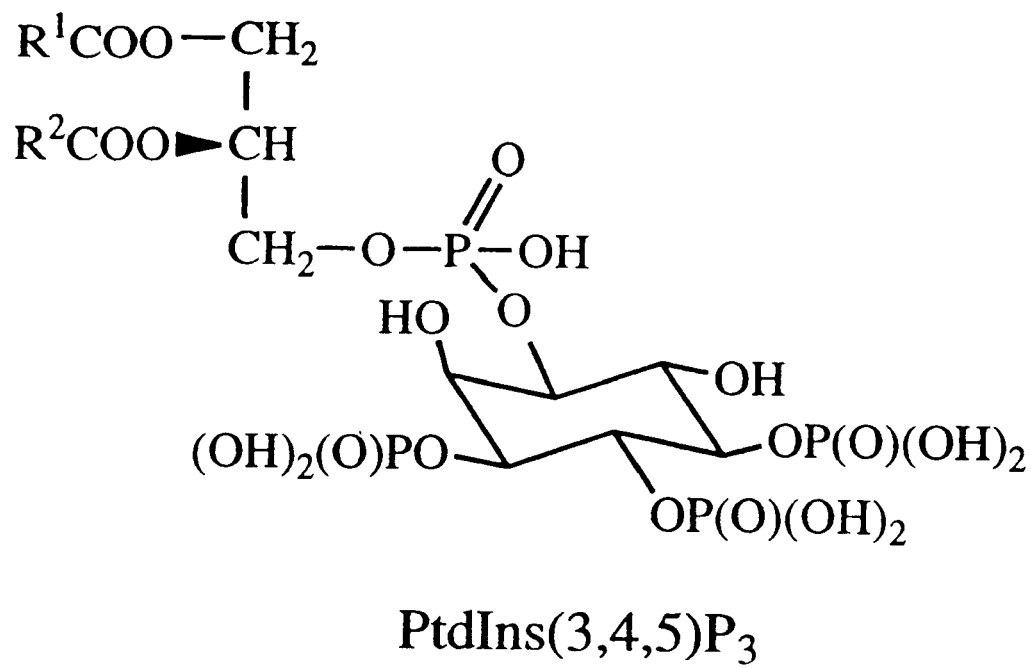
FIG. 3 illustrates retrosynthetic analysis of the D-3-phosphorylated phosphoinositide PtdIns(3,4,5)P$_3$ for synthesis from PtdIns(4,5)P$_2$.
Figure 3:
Figure 3:
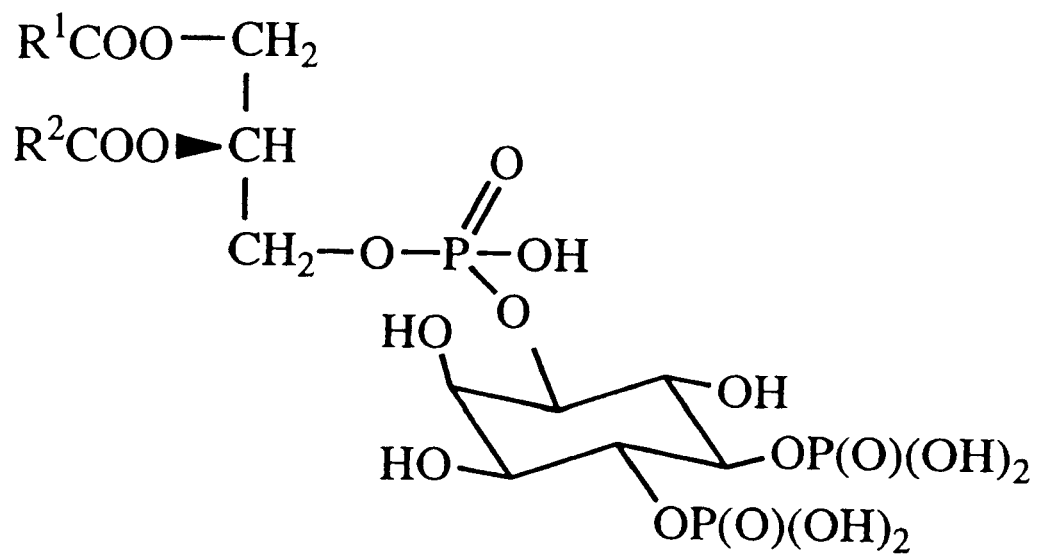
Figure 4:
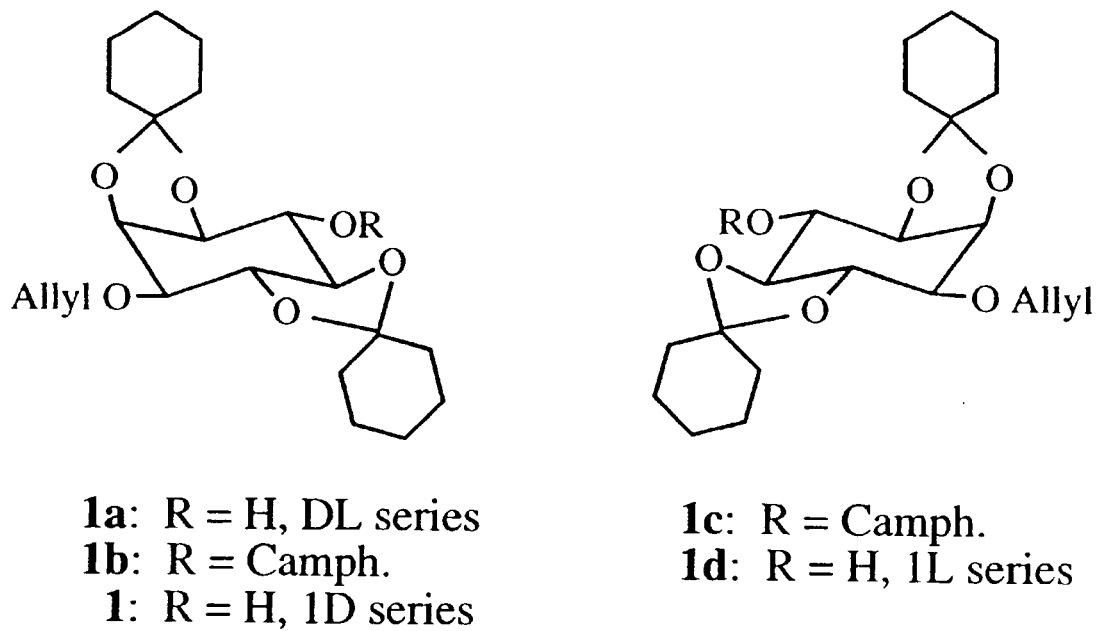
FIG. 4 Preparation of 1D-1,2:4,5-di-O-cyclohexylidene-3-O-allyl-myo-inositol (−)-1 starting material.

The cellular 3-PPI all belong to the 1D-myo-inositol stereochemical series. The present approach to synthesis uses 1D-1,2:4,5-di-O-cyclohexylidene-3-O-allyl-myo-inositol (−)-1 as purposely designed starting material and 1D-1,2-O-cyclohexylidene-3-O-allyl-6-O-benzyl-myo-inositol (+)-3 as a key myo-inositol synthon. For the preparation of the starting material (FIG. 4), reaction of highly purified (±)-1,2:4,5-di-O-cyclohexylidene-myo-inositol (8) and allyl bromide in DMF at 0–5° C. with gradual addition of NaH as a new protocol providing kinetic control, resulted in highly selective mono-allylation at 3-OH, such that (±)-1,2:4,5-di-O-cyclohexylidene-3-O-allyl-myo-inositol 1a (9) was obtained pure by crystallization without need for liquid chromatography. Esterification of the (±)-3-O-allyl derivative using (1s)-(−)-camphanic acid chloride/NEt$_3$ and separation of the diastereomeric esters by MPLC on silica and crystallization from acetone gave each of the two diastereomers (>80% yield) in >98% purity as judged by TLC, HPLC and $^1$H NMR. Alkali catalyzed hydrolysis of the more polar of the two diastereomeric esters 1b, |α|$_D$ −16.5°, (c 1.5 CHCl$_3$) yielded (−)-1, |α|$_D$ −9.5°, (c 1.0, CHCl$_3$). Similar treatment of the less polar diastereomer 1c, |α|$_D$ −2.03°, (c 1.0 CHCl$_3$) gave (+)-1d, |α|$_D$ +9.17°, (c 0.5, CHCl$_3$). The absolute configuration of each enantiomer was established as follows. Reaction of (−)-1 successively with (i) hot HOAc—H$_2$O to remove both the O-cyclohexylidene protecting groups, and (ii) an excess of NaH and BnBr in anhydrous DMF, gave 1D-3-O-allyl-1,2,4,5,6-penta-O-benzyl-myo-inositol, |α|$_D$ −2.3°, (c 1.0, CHCl$_3$). Treatment of the O-benzyl derivative with potassium tert-butoxide in warm DMSO to isomerize O-allyl to O-|prop-1'-enyl| followed by methanolic HCl (10) yielded (+)-1,2,4,5,6-penta-O-benzyl-myo-inositol, |α|$_D$ +11.2°, (c 1.1, CHCl$_3$). The absolute configuration of (+)-1,2,4,5,6-penta-O-benzyl-myo-inositol has been unequivocally assigned as 1D-1,2,4,5,6-penta-O-benzyl-myo-inositol (11). Therefore, the absolute configuration of (−)-1 is derived unambiguously as 1D-1,2:4,5-di-O-cyclohexylidene-3-O-allyl-myo-inositol. Similarly, (+)-1d is assigned the 1L-configuration.

Figure 5:
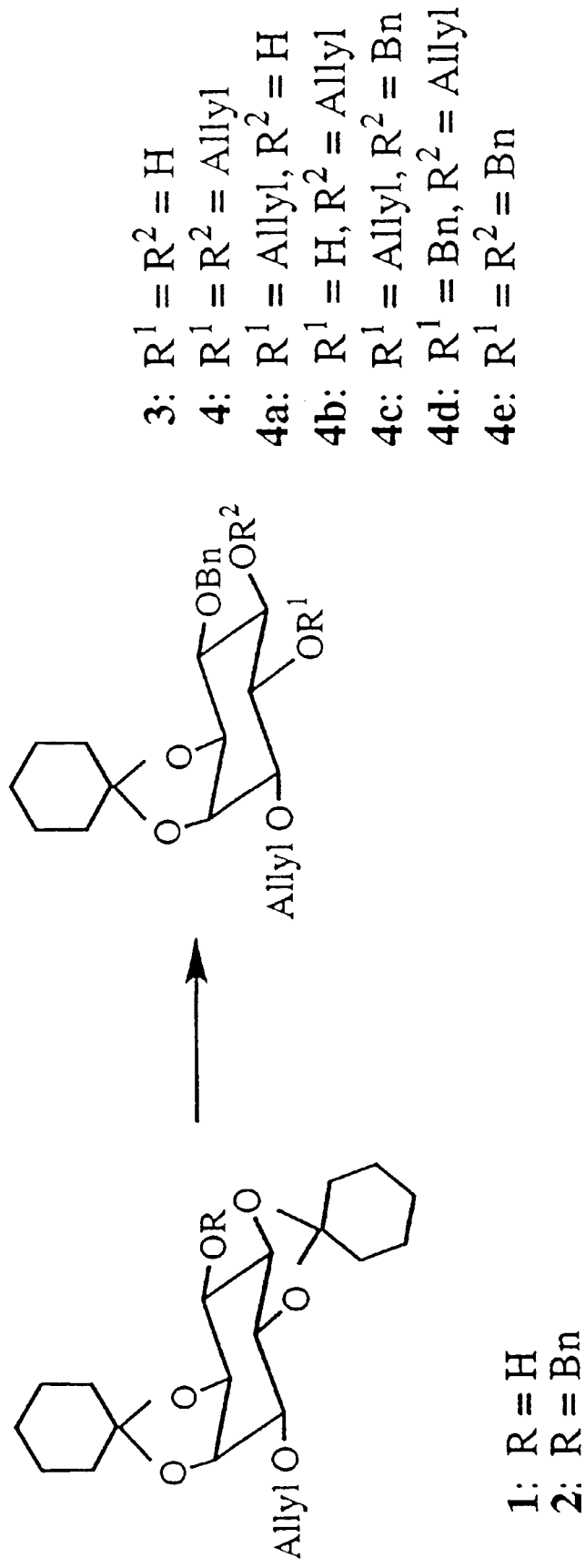
FIG. 5 Preparation and structures of key myo-inositol intermediates.

In the first step of synthesis (FIG. 5), reaction of (−)-1 with excess BnBr/NaH in DMF at R.T. overnight gave in quantitative yield its 6-O-benzyl derivative (−)-2 |α|$_D$ −51.6° (c 1.1, CHCl$_3$). Transketalization under kinetic control by reaction of (−)-2 with ethylene glycol (1.2 mole)/ catalytic p-TSA in CH$_2$Cl$_2$ at R.T. for 3 hr. gave the key synthon (+)-3, yield 81%, |α|$_D$ +26.2° (c 1.0, CHCl$_3$). Reaction of (+)-3 in DMF at R.T. for 8 hr. with 1.2 moles of allyl bromide and NaH yielded the complete set of intermediates required for all four known PtdIns-3-phosphates. By chromatography on silica, the following pure compounds were obtained (FIG. 5): in 28% yield, 1D-1,2-O-cyclohexylidene-3,4,5-tri-O-allyl-6-O-benzyl-myo-inositol (−)-(4) |α|$_D$ −11.3° (c 1.0, CHCl$_3$), Lit. |α|$_D$ −9.2°, (c 1.5, CHCl$_3$) (12); in 26% yield, 1D-1,2-O-cyclohexylidene-3,4-di-O-allyl-6-O-benzyl-myo-inositol (+)-(4a), |α|$_D$ +11.6° (c 0.82, CHCl$_3$); in 24% yield, 1D-1,2-O-cyclohexylidene-3,5-di-O-allyl-6-O-benzyl-myo-inositol (−)-(4b) |α|$_D$ −13.5° (c 0.96, CHCl$_3$); and, in 22% yield, unchanged starting material (+)-3. The overall utilization of (+)-3 is 90% considering that the recovered compound is converted into (−)-4e in the next step (complete benzylation). Alternatively, reaction of (+)-3 as above but using an excess of allyl bromide/NaH yielded (−)-(4) in quantitative yield. Compounds (+)-4a, (−)-4b, and (+)-3 each were treated with an excess of BnBr and NaH in DMF at R.T. for 16 hr. and gave quantitative yields of the fully O-protected myo-inositols (−)-4c |α|$_D$ −5.6° (c 1.43, CHCl$_3$), (−)-4d |α|$_D$ −21.3° (c 1.23, CHCl$_3$), and (−)-4e |α|$_D$ −25.3° (c 2.0, CHCl$_3$).

Figure 6A:
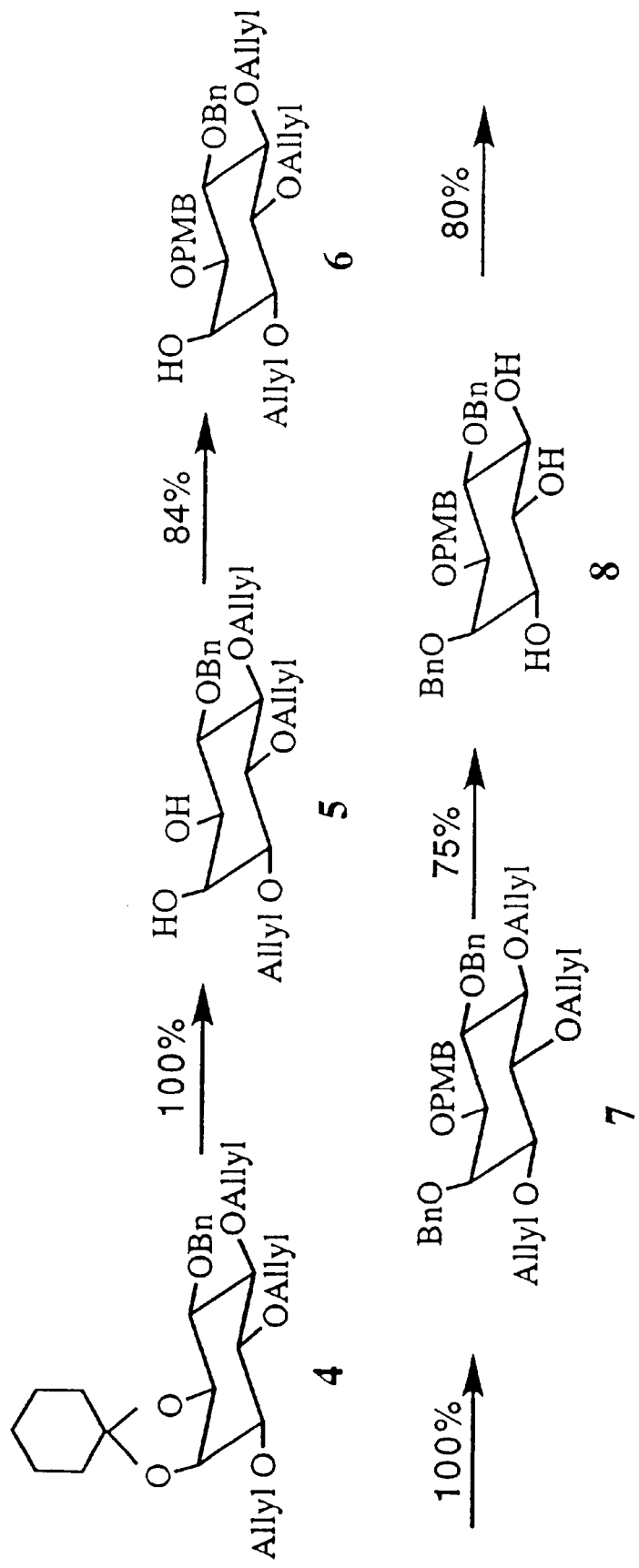
FIGS. 6A, 6B and 6C Synthesis of selectively protected myo-inositol synthons and PtdIns(3,4,5)P$_3$.
Figure 6B:
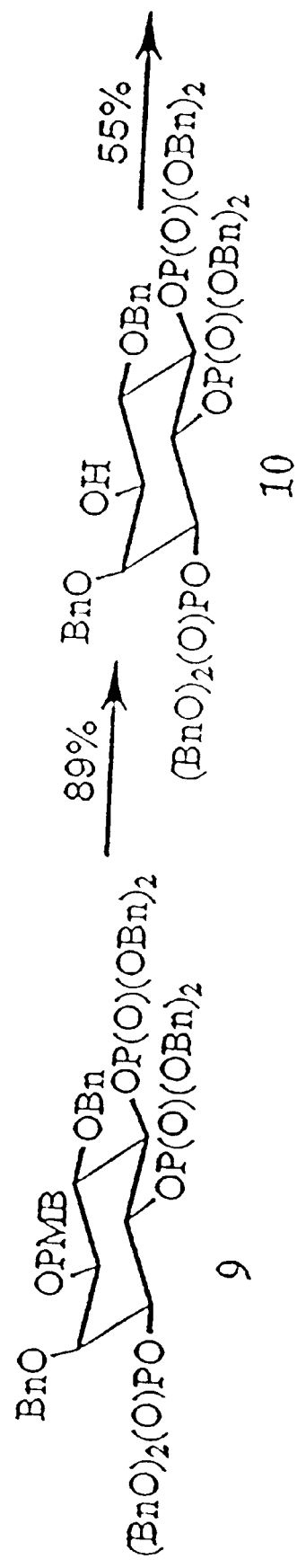
Figure 6C:
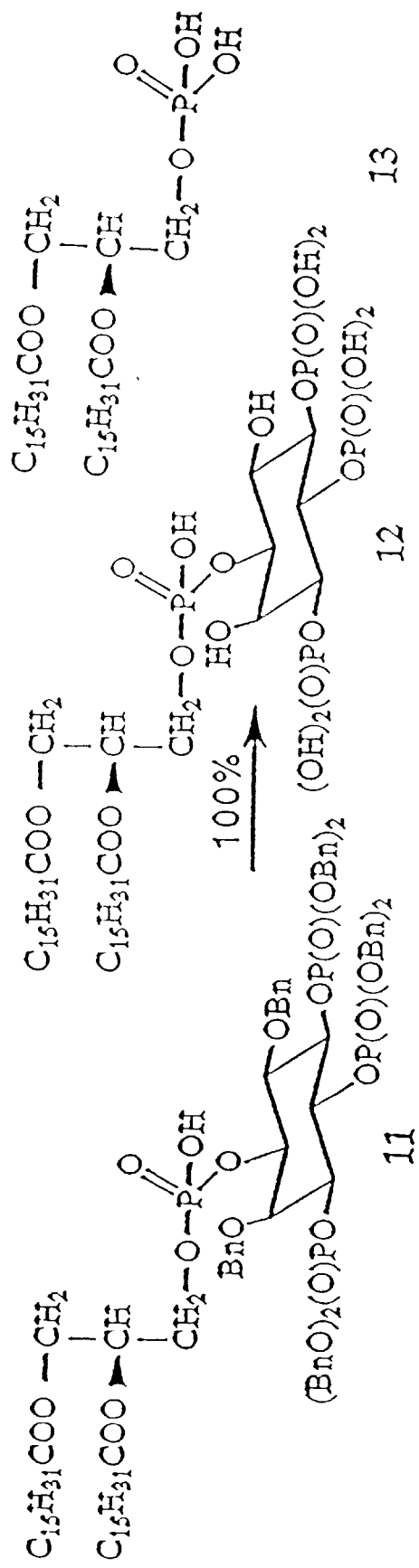

Compounds (−)-4, (−)-4c, (−)-4d, and (−)-4e are intermediates respectively for the synthesis of PtdIns(3,4,5)P$_3$, PtdIns(3,4)P$_2$, PtdIns(3,5)P$_2$, and PtdIns(3)P, by the sequence of reactions illustrated for PtdIns(3,4,5)P$_3$ series (FIG. 6A, 6B and 6C). On heating at 95° C. for 3 hr. with acetic acid-water (80:20), (−)-4 lost the O-cyclohexylidene protection and gave the 1,2-diol (−)-5 |α|$_D$ −16.2° (c 1.0, CHCl$_3$), Lit. |α|$_D$ −10° (c 2, CHCl$_3$). Reaction of (−)-5 with Bu$_2$SnO in toluene with azeotropic removal of H$_2$O, rotary evaporation, solvent change to DMF and treatment with 4-methoxybenzyl chloride at 50° C. for 8 hr. provided high selectivity for reaction at the equatorial 1-OH over axial 2-OH (91:9) and gave after chromatography on silica (+)-6 |α|$_D$ +6.8° (c 1.0, CHCl$_3$). On treatment with excess BnBr/ NaH in DMF at R.T. for 16 hr., (+)-6 produced 1D-1-O-(4'-methoxybenzyl)-3,4,5-O-tri-O-allyl-2,6-di-O-benzyl-myo-inositol (−)-7 |α|$_D$ −8.0° (c 1.0, CHCl$_3$). Compound (−)-7 incorporates 3 types of blocking groups arranged for selective and successive deblocking and liberation of hydroxyls, from O-allyls for dibenzylphos-phorylation, from the 1-O-(4'-methoxybenzyl) for phosphatidylation, and the O-benzyls to regenerate the free hydroxyls in the target structure. Reaction of (−)-7 with 10% Pd—C in methanol-acetic acid-water (98:2:0.1) under reflux caused complete O-deallylation to yield (−)-8 |α|$_D$ −7.5° (c 1.0, CHCl$_3$). Reaction of (−)-8 in DMF with NaH and tetrabenzyl pyrophosphate (13) produced the 3,4,5-tris-O-(dibenzyl phosphate) derivative (−)-9 |α|$_D$ −9.5° (c 2.9, CHCl$_3$). The treatment of (−)-9 with DDQ in CH$_2$Cl$_2$ yielded the 1D-2, 6-O-dibenzyl-myo-inositol 3,4,5-tris-(dibenzylphosphate) (−)-10 |α|$_D$ −6.5° (c 0.2, CHCl$_3$), a key intermediate for the preparation of PtdIns(3,4,5)P$_3$. The same sequence of reactions as described above for compound (−)-4 (FIG. 6A, 6B and 6C), carried out with (−)-4c, (−)-4d, and (−)-4e, gave 10c, 10d, and 10e as the corresponding intermediates respectively for the preparation of PtdIns(3,4)P$_2$, PtdIns(3,5)P$_2$, and PtdIns(3)P.

The next step in this synthesis is the condensation of the selectively protected 1D-myo-inositol derivative (−)-10, 10c, 10d, or 10e with the lipid sn-3-phosphatidic acid. Methods for the preparation of sn-3-phosphatidic acids are well known in the literature and in fact sn-phospahtidic acids with a variety of fattyacyls are available from commercial sources.

Reaction of (−)-10 with 1,2-dihexadecanoyl-sn-glycero-3-phosphoric acid (14) (13) in anhydrous pyridine and triisopropyl-benzenesulfonyl chloride as condensing agent (15) at R.T. for 18 hr. gave the phosphodiester product 1D-1-(1',2'-dihexadecanoyl-sn-glycero-3'-phospho)-myo-inositol-3,4,5-tris-(dibenzylphosphate) (+)-11 $|\alpha|_D$ +4.0° (c 0.3, CHCl$_3$). Hydrogenolysis of (+)-11 in ethanol using Pd-black and H$_2$ gas at 45 psi yielded 1-(1',2'-dihexadecanoyl-sn-glycero-3'-phospho)-myo-inositol-3,4,5-trisphosphate, PtdIns(3,4,5)P$_3$, (+)-12 $|\alpha|_D$ +5.8° (c 0.2, CHCl$_3$—MeOH—H$_2$O, 2:1:0.1). Lit. $|\alpha|_D$ +3.7 (c 0.5, CHCl$^3$).[5b]

The present choice of preformed sn-3-phosphatidic acid as the lipid synthon merits special comment. It contrasts with the related syntheses which all utilize sn-1,2-diacylglycerol in tetrazole-catalyzed reaction with (benzyloxy)bis(N,N-diisopropylamino)-phosphine, BnOP(NCH(CH$_3$)$_2$)$_2$, or related phosphoramidite (5). The use of sn-3-phosphatidic acid prepared from natural sn-glycero-3-phosphocholine avoids problems endemic to the chemistry of 1,2-diacylglycerol. The latter isomerize readily via neighboring O-acyl migration to equilibrium mixtures comprising the 1,2-, 1,3- and 2,3-diacylglycerols (16), and indeed 1,3-dihexadecanoyl-glycerol is detected by TLC in the tetrazole-catalyzed reaction of sn-1,2-dihexadecanoylglycerol with BnOP(NCH(CH$_3$)$_2$)$_2$ (17). This equilibration is tantamount to racemization which is virtually complete for the reaction of sn-1,2-dihexanoylglycerol. Such propensity for racemization is absent from sn-3-phosphatidic acids. This is critically important for synthesis of PtdIns-3-phosphates with hexanoyl or shorter chain acyls.

In contrast with the long chain acyl derivatives which are self-aggregating in water, the short chain analogues are expected to form monomeric solutions and are considered advantageous as biochemical probes (3,4). The absolute configuration of sn-3-phosphatidic acids is well established, and that of the key myo-inositol synthon is derived unequivocally based on their preparation from (−)-1. The one-step esterification of the sn-3-phosphatidic acid and the myo-inositol synthon is stereochemically innocuous. Thus, the present approach ensures that the structural and sterochemical integrity of the lipid and the myo-inositol synthons is conveyed faithfully and unambiguously to the target phosphatidylinositol-3-phosphates.

Partial Synthesis of PtdIns(3,4,5)P$_3$ from PtdIns(4,5)P$_2$

Figure 7A:
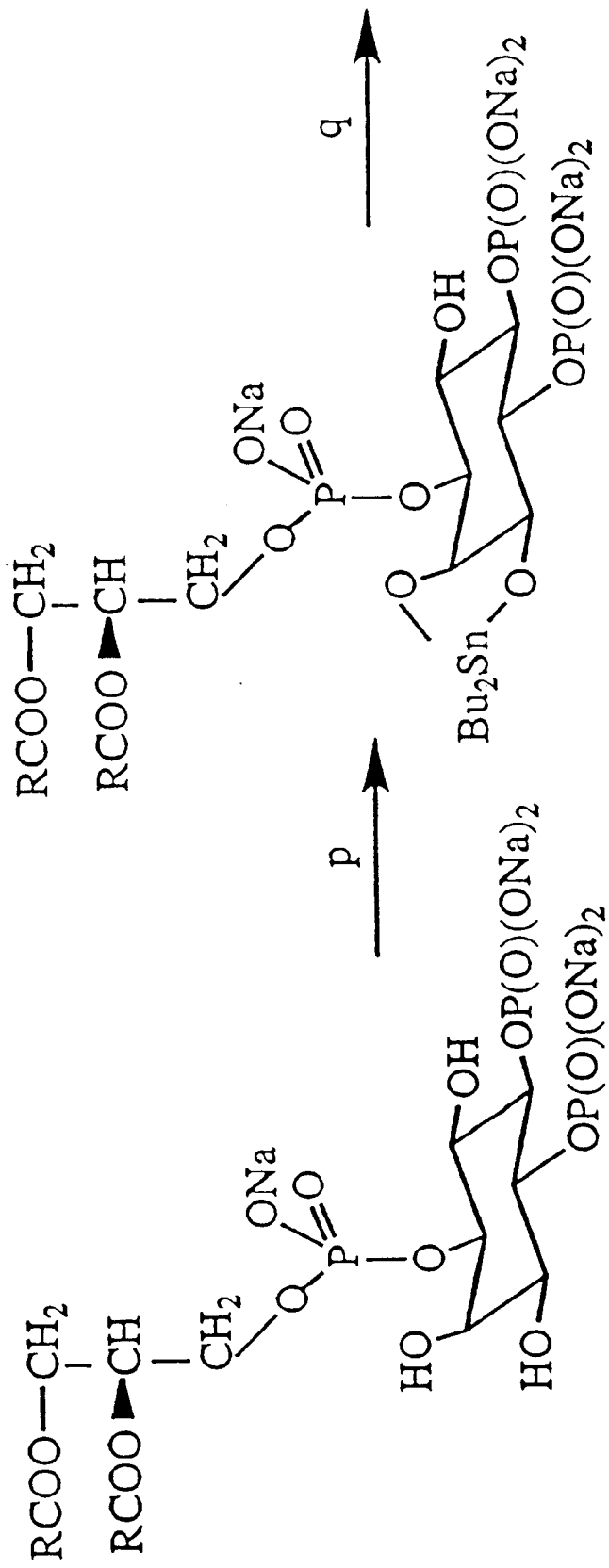
FIG. 7A and 7B Partial Synthesis of PtdIns(3,4,5)P$_3$ from PtdIns(4,5)P$_2$.
Figure 7B:
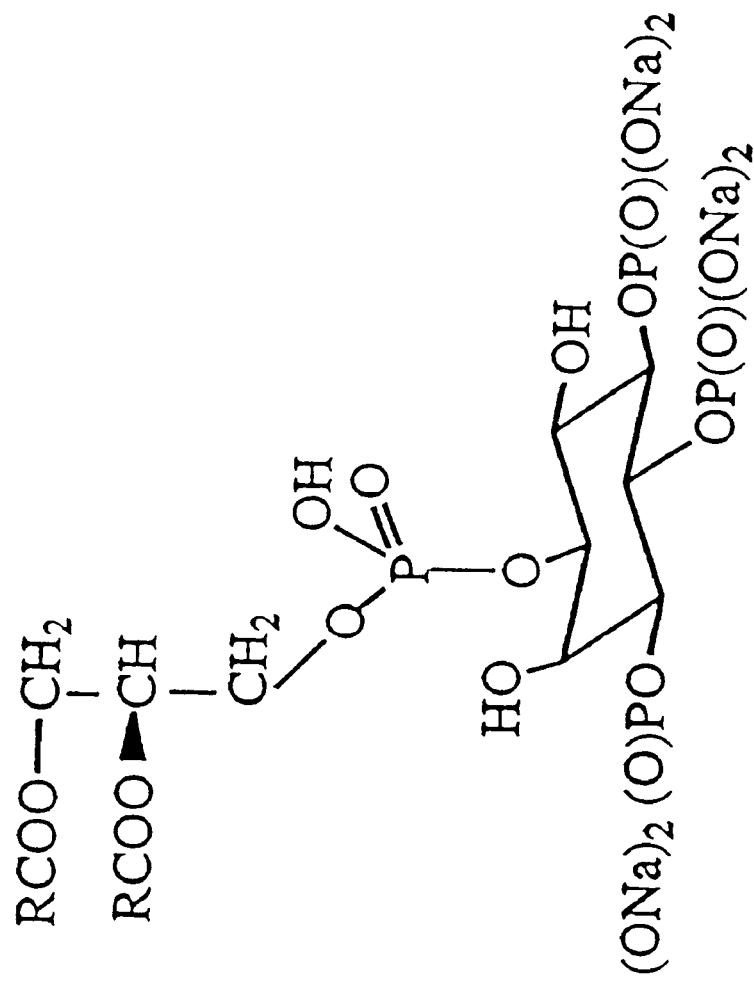

The partial synthesis of 3-PPI by regioselective phosphorylation at 3-OH in preformed phosphoinositides (FIG. 7) is illustrated by the regioselective phosphorylation at 3-OH of PtdIns(4,5)P$_2$. A 2,3-dibutylstannylene derivative was formed in situ by reaction with dibutyltin oxide followed by reaction with dibenzyl chlorophosphate without overt blocking of other alcoholic hydroxyls in the molecule. Purification followed by removal of benzyl protection by hydrogenation gave PtdIns(3,4,5)P$_3$, identical in TLC comparison with the product (+)-12 but different from PtdIns(2,4,5)P$_3$ obtained by unequivocal synthesis from 1D-1-(1',2'-dihexadecanoyl-sn-glycero-3'-phospho)-3,6-dibenzyl-myo-inositol-4,5-bis(dibenzylphosphate).

Figure 8:
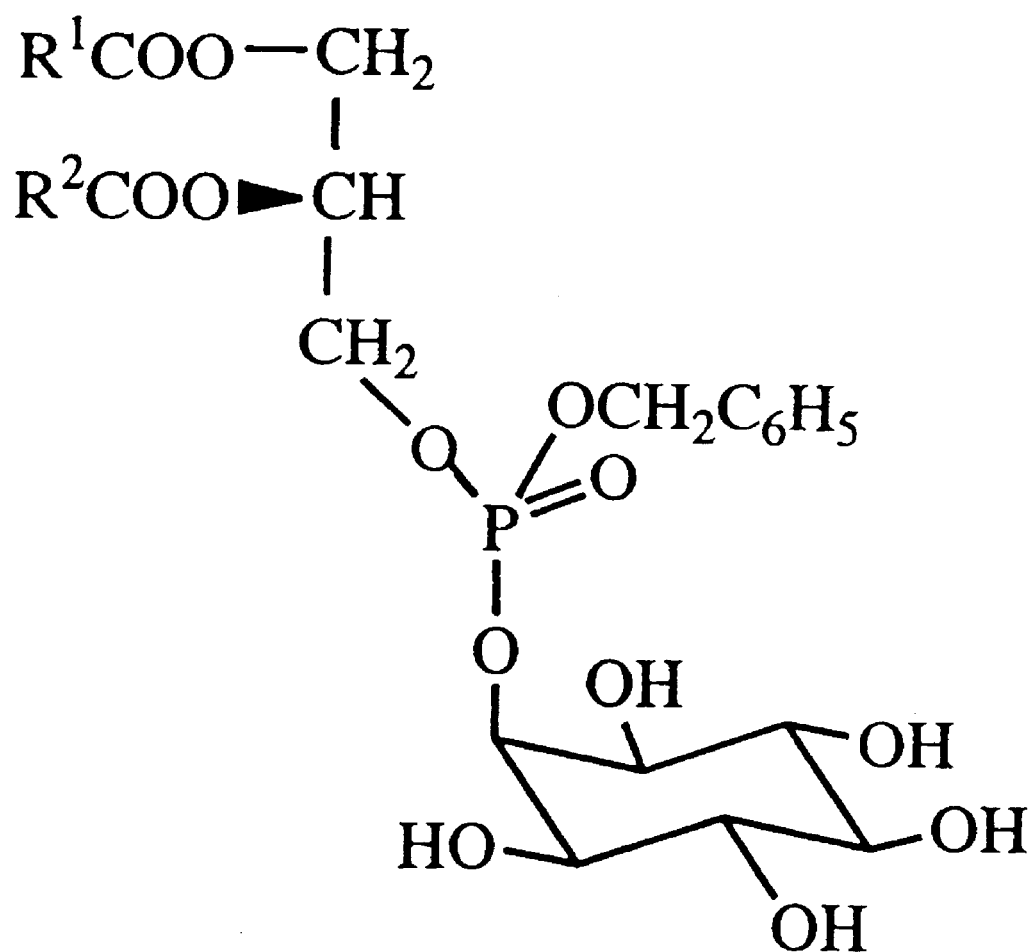
FIG. 8 PtdIns-benzyl ester, starting material for phosphorylation to PtdIns(3)P.

In an alternative approach, the reaction at room temperature between PtdIns-benzyl ester (FIG. 8) in anhydrous pyridine with 2-trichloroethylphosphoric acid using triisopropyl-benzenesulphonyl chloride gave a mixture. With 0.1 mol proportion of 2-trichloroethylphosphoric acid, a single product was formed. On treatment with activated zinc and acetic acid to remove the 2-trichloroethyl protecting group, followed by NaI in anhydrous acetone for anionic debenzylation, a mixture of unchanged PtdIns and PtdIns (3)P was obtained, and separated by liquid chromatography on aminiopropylsilica column.

The product distribution in the phosphorylation of PtdIns-benzyl ester described above was controlled experimentally by varying the mol proportion of the reactants to obtain concurrently all possible 3-PPI structures as phosphoinositide "libraries". The individual 3-PPI as well as the "libraries" have immense potential value as probes in bioactivity screens. Other direct or indirect phosphorylation reagents and protocols may be utilized for the phosphorylation step.

EXAMPLE 1

1D-1-(1,2-Dihexadecanoyl-sn-glycero-3'-phospho)-myo-inositol-3,4,5-trisphosphate, PtdIns(3,4,5)P$_3$, (+)-12

(±)-1:2:4,5-Di-O-cyclohexylidene-3-O-allyl-myo-inositol (1a)

To a solution of 105 g (0.309 mol) of DL-1,2:4,5-di-O-cyclohexylidene-myo-inositol in 400 ml DMF, 26 ml (0.30 mol) allyl bromide (from a dropping funnel) was added under N$_2$ at 0–5° C. and 16.6 g (0.415 mol, 40% oil) NaH was added gradually. Reaction was left at R.T. overnight. TLC (solvent: CH$_2$Cl$_2$/ether 95:5) showed D,L-1:2:4,5-Di-O-cyclohexylidene-3-O-allyl-myo-inositol as the major product. Excess NaH was destroyed with DH$_2$O at 0–5° C. DMF and H$_2$O were evaporated. Residue was extracted with CHCl$_3$,dried, filtered and concentrated. Crude reaction product crystallized three times from acetone gave pure DL-1:2:4,5-di-O-cyclohexylidene-3-O-allyl-myo-inositol (1a). (76.3 g, 65%).

1D-1,2:4,5-Di-O-cyclohexylidene-3-O-allyl-6-O-camphanate-myo-inositol (1b)

To a solution of 25.5 g(0.067 mol) of D,L-1:2:4,5-di-O-cyclohexylidene-3-O-allyl-myo-inositol (1a) in 200 ml CH$_2$Cl$_2$, 10 ml triethylamine and 16.0 g (0.074 mol) of (1S)-(−)-camphanic acid chloride in CH$_2$Cl$_2$ (from a dropping funnel) were added at 0–5° C. Reaction was left at R.T. overnight. TLC (solvent: hexane/ethyl acetate 80:20) showed reaction was complete. Reaction was neutralized, extracted, dried, filtered and concentrated. Crude reaction was chromatographed on silica gel, 200–425 MESH) eluted with a gradient of hexane/CH$_2$Cl$_2$/ethyl acetate followed with crystalization gave pure 1D-1,2:4,5-di-O-cyclohexylidene-3-O-allyl-6-O-camphanate-myo-inositol (1b). (37.5 g, 100%) $|\alpha|_D$=−16.5° (c 1.5, CHCl$_3$).

1D-1,2:4,5-Di-O-cyclohexylidene-3-O-allyl-myo-inositol (1)

To 14.2 g (25.3 mmol) of 1D-1,2:4,5-di-O-cyclohexylidene-3-O-allyl-6-O-camphanate-myo-inositol (1b), 500 ml ether, 500 ml ethanol, 100 mg (0.29 mmol) of tetrabutyl ammonium hydrogen sulfate and 3.35 g (79.8 mmol) lithium hydroxide (in 30 ml $DH_2O$, from a dropping funnel) were added. Reaction was left at R.T. overnight. TLC (solvent: $CH_2Cl_2$/ether 95:5) showed reaction was complete. Ether and ethanol were evaporated. Residue was extracted, dried, filtered and concentrated. Crude reaction was passed through a short column, eluted with $CHCl_3$, gave pure 1D-1,2:4,5-di-O-cyclohexylidene-3-O-allyl-myo-inositol (1). (9.6 g,100%) $|\alpha|_D$=–9.5° (c 1.0, $CHCl_3$).

1D-1,2:4,5-Di-O-cyclohexylidene-3-O-allyl-6-O-benzyl-myo-inositol (2)

To a solution of 8.64 g (23 mmol) of 1D-1,2:4,5-di-O-cyclohexylidene-3-O-allyl-myo-inositol (1) in 180 ml DMF, 3.2 g (80 mmol, 40% oil) NaH and 4 ml (33.6 mmol), from a dropping funnel) benzyl bromide were added under $N_2$ at 0–5° C. Reaction was left at R.T. overnight. TLC (slovent: hexane/ethyl acetate 80:20) showed reaction was complete. Excess NaH was destroyed with $DH_2O$ at 0–5° C. DMF and $H_2O$ were evaporated, residue was extracted, dried, filtered and concentrated. Crude reaction was chromatographed on silica gel (200–425MESH) eluted with a gradient of hexane/ethyl acetate gave pure 1D-1,2:4,5-di-O-cyclohexylidene-3-O-allyl-6-O-benzyl-myo-inositol (2). (10.8 g, 100%) $|\alpha|_D$=–51.6° (c 1.1, $CHCl_3$).

1D-1,2-O-Cyclohexylidene-3-O-allyl-6-O-benzyl-myo-inositol (+)-3

To a solution of 6.1 g (13.0 mmol) of 1D-1,2:4,5-di-O-cyclohexylidene-3-O-allyl-6-O-benzyl-myo-inositol (2) in 65 ml $CH_2Cl_2$ (dried over $P_2O_5$ for 1 hr), 0.5 ml (8.97 mmol) of ethylene glycol and 48 mg (0.252 mmol) of p-toluenesulfonic acid were added under $N_2$ at R.T. After 2 hrs, TLC (solvent: $CH_2Cl_2$/acetone 95:5, product Rf: 0.2) showed reaction was complete. 5 drops of triethylamine, 15 drops of $DH_2O$ and 1.0438 g (11.9 mmol) of $KHCO_3$ were added to the flask. Reaction was later diluted with 200 ml $CH_2Cl_2$, filtered, dried, filtered again and concentrated. Crude reaction was chromatographed on silica gel (200–425 MESH) eluted with a gradient of hexane/ethyl acetate gave pure1D-1,2-O-cyclohexylidene-3-O-allyl-6-O-benzyl-myo-inositol (3). (4.1 g, 81%) $|\alpha|_D$=+26.2° (c 1.0, $CHCl_3$). $^1$H-NMR (300 MHz, $CDCl_3$): δ ppm 1.54–1.71 (br m, 10H, cyclohex-), 2.7 (br, 2H, OH), 3.38 (ψt, J 9.6 Hz, 1H, H-5), 3.41–3.56 (m, 2H, H-3 & H-6), 3.89 (ψt, J 9.4 Hz, 1H, H-4), 4.01–4.15 (m, 1H, H-1), 4.16–4.28 (m, 2H, $CH_2$—C=), 4.38 (dd, J 4.2, 4.2 Hz, 1H, H-2), 4.81 (q, 2H, J 11.4 & 91.8, Phenyl-$CH_2$), 5.19–5.34 (m, 2H, $CH_2$=C), 5.89–6.03 (m, 1H, —CH=C), 7.24–7.38 (m, 5H, $C_6H_5$). In diacetate of (+)-3, 3.89 H-4, 3.38 H-5 signals shift to 5.30 and 4.99.

1D-1,2-O-Cyclohexylidene-3,4,5-tri-O-allyl-6-O-benzyl-myo-inositol (4)

To a solution of 2.4 g (6.1538 mmol) of 1D-1,2-O-cyclohexylidene-3-O-allyl-6-O-benzyl-myo-inositol (3) in 50 ml DMF, 1.24 g (31 mmol, 40% oil) of NaH and 2 ml (23.0 mmol) of allyl bromide were added under $N_2$ at 0–5° C. Reaction was left at R.T. overnight. TLC (solvent: hexane/ethyl acetate 80:20) showed reaction was complete. Excess NaH was destroyed with $DH_2O$ at 0–5° C. Reaction was extracted with $CHCl_3$, dried, filtered and concentrated. Crude reaction was chromatographed on silica gel (200–425 MESH) eluted with a gradient of hexane/$CH_2Cl_2$/ethyl acetate gave pure1D-1,2-O-cyclohexylidene-3,4,5-tri-O-allyl-6-O-benzyl-myo-inositol (4). (2.9 g, 100%) $|\alpha|_D$=–11.3° (c 1.0, $CHCl_3$).

Reaction of (+)-3 in DMF at R.T. for 8 hr. with 1.2 moles of allyl bromide and NaH yielded the complete set of intermediates required for all four known PtdIns-3-phosphates. By chromatography on silica, the following pure compounds were obtained (FIG. 5): in 28% yield, 1D-1,2-O-cyclohexylidene-3,4,5-tri-O-allyl-6-O-benzyl-myo-inositol (–)-(4) $|\alpha|_D$ –11.3° (c 1.0, $CHCl_3$). Lit. $|\alpha|_D$ –9.2°, (c 1.5, $CHCl_3$); in 26% yield, 1D-1,2-O-cyclohexylidene-3,4-di-O-allyl-6-O-benzyl-myo-inositol (+)-(4a), $|\alpha|_D$ +11.6° (c 0.82, $CHCl_3$); in 24% yield, 1D-1,2-O-cyclohexylidene-3,5-di-O-allyl-6-O-benzyl-myo-inositol (–)-(4b)[10] $|\alpha|_D$ –13.5° (c 0.96, $CHCl_3$); and, in 22% yield, unchanged starting material (+)-3. The structures of the two monobenzyl derivatives were established by NMR spectra below.

(+)-4a. $^1$H-NMR (300 MHz, $CDCl_3$): δ ppm 1.17–1.74 (br m, 10H, cyclohex-), 2.64 (br, 1H, OH), 3.44 (ψt, J 9.5 Hz, 1H, H-5), 3.56–3.68 (m, 2H, H-3 and H-6), 4.12 (ψt, J 5.9 Hz, 1H, H-4), 4.17–4.21 (m, 1H, H-1), 4.17–4.32 (m, 4H, 2 $CH_2$—C=), 4.35 (dd, J 4.2, 4.2 Hz, 11H, H-2), 4.80 (q, 2H, J 12.0 and 57.0, Phenyl-$CH_2$), 5.13–5.32 (m, 4H, 2 $CH_2$=C), 5.85–5.97 (m, 2H, -2 CH=C), 7.18–7.38 (m, 5H, $C_6H_5$). In the monoacetate of (+)-4a, the 3.44 H-5 signal shifts downfield to 4.93.

The $^1$H-NMR of (–)-4c, the O-benzyl derivative of (+)-4a, was identical with the spectrum of DL-4c prepared by complete benzylation, selective removal of 3,4-O-cyclohexylidene, and complete allylation from DL-1,2:3,4-di-O-cyclohexylidene-myo-inositol (Garegg, P. J; Iversen, T.; Johansson, R.; Lindberg, B. Carbohydr. Res. 1984, 130, 322–326)|.

(–)-(4b) $^1$H-NMR (300 MHz, $CDCl_3$): δ ppm 1.34–1.72 (br m, 10H, cyclohex-), 2.59 (br, 1H, OH), 3.16 (ψt, J 9.4 Hz, 1H, H-5), 3.48 (q, J 9.6 and 3.7, 1H, H-3), 3.62 (ψt, J 6.6 Hz, 1H, H-6), 3.93 (ψt, J 9.5 Hz, 1H, H-4), 4.11 (q, J 5.2 and 7.0 Hz, 1H, H-1), 4.17–4.38 (m, 4H, 2 $CH_2$—C=), 4.41 (dd, J 4.1, 1.1 Hz, 1H, H-2), 4.80 (q, 2H, J 11.4 and 35.4, Phenyl-$CH_2$), 5.13–5.34 (m, 4H, 2 $CH_2$=C), 5.87–5.98 (m, 2H, 2 —CH=C), 7.23–7.38 (m, 5H, $C_6H_5$). In the monoacetate of (–)-4b, 3.93 H-4 signal is shifted downfield to 5.33 and the latter shows spin connectivity to 3.28 H-5 and 3.58 H-3 signals observed by selective irradiation at 5.58 and $^1$H COSY (500 MHz).

1D-3,4,5-Tri-O-allyl-6-O-benzyl-myo-inositol (5)

To 4.4 g (9.36 mmol) of 1D-1,2-O-cyclohexylidene-3,4,5-tri-O-allyl-6-O-benzyl-myo-inositol (4), 80% aqueous acetic acid was added, reaction was heated at 90° C. for several hrs. TLC (solvent: $CHCl_3$/MeOH 95:5) showed the conversion was complete. Reaction was then neutralized (with $KHCO_3$),extracted (with $CHCl_3$), dried, filtered and concentrated. Crude reaction was chromatographed on silica gel (200–425 MESH) eluted with a gradient of $CHCl_3$/MeOH to give pure 1D-3,4,5-tri-O-allyl-6-O-benzyl-myo-inositol (5). (3.65 g,100%) $|\alpha|_D$=–16.2° (c 1.01 $CHCl_3$).

1D-3,4,5-Tri-O-allyl-6-O-benzyl-1-(p-methoxybenzyl)-myo-inositol (6)

A mixture of 3.65 g (9.3 mmol) of 1D-3,4,5-tri-O-allyl -6-O-benzyl-myo-inositol (5), 2.65 g (1.06 mmol) of $Bu_2SnO$ and 50 ml toluene was heated under reflux, with azeotropic removal of water, for 2 hrs. Mixture was heated under reflux for 1 more hr after adding 150 mg (0.44 mmol) of tetrabutyl ammonium hydrogen sulfate. Toluene was then evaporated and 50 ml DMF along with 2.55 ml (1.88 mmol) of 4-methoxybenzyl chloride were added. Reaction was heated at 108–110° C. for several hrs. TLC (solvent: CH$_2$Cl$_2$/acetone 95:5 product Rf:0.4) showed reaction was complete. DMF was evaporated and residue was extracted, dried, filtered and concentrated. Crude reaction was chromatographed on silica gel (200–425 MESH) eluted with a gradient of hexane/CH$_2$Cl$_2$/ethyl acetate gave pure 1D-3,4,5-tri-O-allyl-6-O-benzyl-1-(p-methoxybenzyl)-myo-inositol (6).(3.99 g, 84%) |α|$_D$=+6.8° (c 1.0, CHCl$_3$). (+)-6 $^1$H-NMR (300 MHz, CDCl$_3$): δ ppm 2.54 (br, 1H, OH), 3.05 (dd, J 2.4 and 10.0 Hz, 1H, H-1), 3.13–3.23 (m, 2H, H-3 and H-6), 3.23–3.77 (m, 1H, H-5), 3.73 (s, 3H, OCH$_3$), 3.87 (ψt, J 10.1 Hz, 1H, H-4), 3.97–3.99 (m, 1H, H-2), 4.20–4.28 (m, 6H, 3 CH$_2$—C=), 4.43–4.80 (m, 4H, 2 Phenyl-CH$_2$), 5.05–5.25 (m, 6H, 3 CH$_2$=C), 5.77–5.95 (m, 3H, 3 —CH=C), 6.75–6.79 (m, 2H, aromat-), 7.13–7.35 (m, 7H, aromat-). In the monoacetate of (+)-6, the 3.97–3.99 H-2 signal shifted to 5.56 ppm.

1D-3,4,5-Tri-O-allyl-2,6-di-O-benzyl-1-(p-methoxybenzyl)-myo-inositol (7)

To a solution of 2.728 g (5.68 mmol) of 1D-3,4,5-tri-O-allyl-6-O-benzyl-1-(p-methoxybenzyl)-myo-inositol (6) in 20 ml DMF, 0.623 g (15.57 mmol, 40% oil) NaH, 0.66 ml (5.55 mmol) of benzyl bromide (from a dropping funnel) were added under N$_2$ at 0–5° C. Reaction was left at R.T. under N$_2$ with stirring overnight. Excess NaH was destroyed with DH$_2$O at 0–5° C. DMF and H$_2$O were evaporated. Crude reaction was chromatographed on silica gel (200–425 MESH) eluted with a gradient of hexane/CH$_2$Cl$_2$/ethyl acetate gave pure 1D-3,4,5-tri-O-allyl-2,6-di-O-benzyl-1-(p-methoxybenzyl)-myo-inositol (7).(3.4 g,100%) |α|$_D$=−7.5° (c 1.0, CHCl$_3$).

1D-2,6-Di-O-benzyl-1-(p-methoxybenzyl)-myo-inositol (8)

To a solution of 437.8 mg (0.7296 mmol) of 1D-3,4,5-tri-O-allyl -2,6-di-O-benzyl-1-(p-methoxybenzyl)-myo-inositol (7) in 4 ml DMSO,1.45 g (12.921 mmol) of potassium tert-butoxide was added. Reaction was heated at 55° C. with N$_2$ atmosphere for several hrs. TLC (solvent: hexane/ethyl acetate 85:15 develop twice) showed the starting material had convered into the corresponding propenyl. Reaction was neutralized with 0.1M HCl to PH=7, extracted, dried, filtered and concentrated. MeOH/HOAC (95:5, 8 ml) was added to the first step product, reaction was heated at 70° C. for 2½ hrs. TLC(solvent: CHCl$_3$/MeOH/NH$_4$OH 90:10:1) showed the desired product. Reaction was then filtered and concentrated. Crude reaction was chromatographed on silica gel (200–425 MESH) eluted with a gradient of CHCl$_3$/MeOH gave pure 1D-2,6-di-O-benzyl-1-(p-methoxybenzyl)-myo-inositol (8). (263 mg, 75%) |α|$_D$=−7.5° (c 1.0, CHCl$_3$).

1D-2,6-Di-O-benzyl-3,4,5-tris-dibenzylphosphanate-1-(p-methoxybenzyl)-myo-inositol (9)

To a solution of 169.9 mg (0.3539 mmol) of 1D-2,6-di-O-benzyl-1-(p-methoxybenzyl)-myo-inositol (8) in 10 ml CH$_2$Cl$_2$ (dried over P$_2$O$_5$), 297.5 mg (4.247 mmol) of 1H tetrazole and 0.7 ml (2.1237 mmol) of N,N-diisopropyl dibenzylphosphoramidite were added, reaction was stirred at R.T. for 15 mins. A −40° C. cold bath was prepared and 770 mg(4.462 mmol) of 3-chloroperoxybenzoic acid was added to the reaction in the cold bath, reaction was stirred at 0° C. for 15 mins. TLC (solvent: hexane/ethyl acetate 60:40) showed the reaction was complete. 250 ml of 20% Na$_2$SO$_3$ solution was added, reaction was stirred at R.T. for 40 mins. NaI test was checked (negative). Reaction was then extracted with CH$_2$Cl$_2$, washed with saturated NaHCO$_3$, followed with saturated NaCl solution. CH$_2$Cl$_2$ layer was dried, filtered and concentrated. Crude reaction was chromatographed on silica gel (200–425 MESH) eluted with a gradient of hexane/ethyl acetate gave pure 1D-2,6-di-O-benzyl-3,4,5-tris-dibenzylphosphate-1-(p-methoxybenzyl)-myo-inositol (9).(356.7 mg, 80%) |α|$_D$=−9.5° (c 2.9, CHCl$_3$).

1D-2,6-Di-O-benzyl-3,4,5-tris-dibenzylphosphate-myo-inositol (10)

To 407.2 mg (0.33 mmol) of 1D-2,6-di-O-benzyl-3,4,5-tris-dibenzylphosphate-1-(p-methoxybenzyl)-myo-inositol (9), 150.3 mg (0.662 mmol) of 2,3-dichloro-5,6-dicyano-1, 4-benzoquinone, 12 ml CH$_2$Cl$_2$ and 4 drops of DH$_2$O were added. Reaction was stirred at R.T. for 1 hr. TLC (solvent: CHCl$_3$/ether 80:20) showed reaction was complete. Reaction was diluted with CH$_2$Cl$_2$, washed with cold saturated NaHCO$_3$ solution, followed with cold saturated NaCl solution, CH$_2$Cl$_2$ layer was dried, filtered and concentrated. Crude reaction was chromatographed on silica gel (200–425 MESH), eluted with a gradient of CHCl$_3$/ether gave pure 1D-2,6-di-O-benzyl-3,4,5-tris-dibenzylphosphate-myo-inositol (10). (335.9 mg, 89%) |α|$_D$=−6.5° (c 0.2, CHCl$_3$).

1D-1-(1',2'-dihexadecanoyl-sn-glycero-3'-phospho)-2,6-dibenzyl-myo-inositol-3,4,5-tris (dibenzylphosphate) (+)-11

A solution of the monohydroxy derivative (−)-10 (0.0578 g), 1,2-dihexadecanoyl-sn-glycero-3-phosphoric acid (sn-3-phosphatidic acid-dihexadecanoyl, 13) (0.0761 g) and tri-isopropylbenzenesulfonyl chloride (0.0685 g) in anhydrous pyridine (0.75 ml) was stirred at r.t. for 2.5 hr. Water (1 ml) was added, the mixture stirred for 1 hr and solvent evaporated in a vacuo. The residue, chromatographed on silicagel (HPLC) eluted with a gradient of CHCl$_3$—CH$_3$OH gave the major product 1D-1-(1',2'-dihexadecnoyl-sn-glycero-3'-phospho)-2,6-dibenzyl-D-myo-inositol-3,4,5-tris (dibenzylphosphate) (+)-11, |α|$_D$+4.0° (c 0.3, CHCl$_3$), (0.0685 g, 69%).

1D-1-(1',2'-Dihexadecanoyl-sn-glycero-3'-phospho)-myo-inositol-3,4,5-trisphosphate, PtdIns(3,4,5)P$_3$, (+)-12

Compound (+)-11 (0.0437 g) and Pd black catalyst (0.0855 g) in EtOH-terButanol (1:1, 10 ml) were shaken in H$_2$ (50 psi) in a Parr hydrogenation apparatus for 16 h. The catalyst was filtered and washed with aqueous ethanol. The filtrate and washings were evaporated to dryness in a vacuo and the residue washed with acetone to obtain the acetone insoluble product PtdIns(3,4,5)P$_3$-dihexadecanoyl, (+)-12) as a white powder (0.025 mg, 92%), |α|$_D$ +5.8° (c 0.2, CHCl$_3$—MeOH—H$_2$O, 2:1:0.1).

Partial Synthesis of PtdIns(3,4,5)P$_3$ from PtIns(4,5)P$_2$

The two step reaction between PtdIns(4,5)P$_2$ and dibenzyl chlorophosphate was carried out as one-pot operation as follows. PtdIns(4,5)P$_2$ 24, (in solution in chloroform-methanol-water (2:1:0.1) was treated with an excess of NEt$_3$ and the solvents removed by rotary evaporation under reduced pressure. The resulting triethylammonium salt was dried in a vacuo over KOH pellets. The dried salt was dissolved a mixture of anhydrous methanol and toluene, mixed with dibutyltin oxide (1 mol. equiv.) and heated at 50° C. for 2 hr. The solvents methanol and toluene were evaporated in a vacuum. The methanol-free residue was suspended in anhydrous THF+DMF (1:1) containing anhydrous NEt$_3$ (excess), cooled to −23° C. and stirred under inert gas and a solution of dibenzyl chlorophosphate (excess) in carbon tetrachloride was added dropwise. The reaction was stirred at −23° C. for 5 hr., allowed to warm to 5° C. and treated with and allowed to stand with ice-cold water overnight. The volatiles were removed under reduced pressure, the residue dissolved in chloroform-methanol-0.5 aqueous HCL and the proportions adjusted to 2:2:1.5 to obtain the lipids in the chloroform layer. Analysis of the chloroform layer by TLC using several protocols indicated the presence of products PtdIns(3,45)P$_3$.

REFERENCES AND NOTES 1. (a). Whitman, M.; Downes, C. P.; Keeler, M.; Keller, T.; Cantley L. *Nature* 1988, 332, 644–646. (b). Traynor-Kaplan, A. E.; Harris, A. L.; Thompson, B. L.; Taylor, P.; Sklar, L. A. *Nature* 1988, 334, 353–356.
2. Reviewed in: Carpenter, C. L.; Cantley, L. C. *Current Opinion in Cell Biology* 1996, 8, 153–158.
3. Toker, A.; Meyer, M.; Reddy, K.; Falck, J. R.; Aneja, R.; Aneja, S.; Parra, A.; Burns, D. J.; Cantley, L. C. *J. Biol. Chem.* 1994, 269, 32358–32367.
4. Reviewed in: Duckworth, B. C.; Cantley, L. C. *Lipid Second Messengers-Handbook of Lipid Research*; Plenum Press: New York. 1996, 8, pp. 125–175.
5. Syntheses of PtdIns-3-phosphates: (a) Reference 3; (b) Gou, D. M.; Chen, C. S. *J. Chem. Soc. Chem. Commun.* 1994, 2125–2126; (c) Reddy, K. K.; Saady, M.; Falck, J. R.; Whited, G. J. *J. Org. Chem.* 1995, 3385–3390; (d) Bruzik, K. S.; Kubiak, R. J. *Tetrahedron Lett.* 1995, 36, 2415–2418; (e) Watanabe, Y.; Tomioka, M.; Ozaki, S. *Tetrahedron* 1995, 51, 8969–8976.
6. Freeman, I. P.; Morton, I. D., *J. Chem. Soc.* 1966, 1710–1714. Serdarevich, B. *J. Amer. Oil Chemists' Soc.* 1967, 44, 381–385.
7. The fattyacyl composition of the cellular PtdIns-3-phosphates is presumed to be identical with cellular PtdIns(4,5)P$_2$; reference 1a.
8. Aneja, R.; Aneja, S. G.; Parra, A. *Tetrahedron Asymmetry* 1995 (No. 1), 17–18.
9. Shashidhar, M. S.; Keana, F. W.; Volwerk, J. J.; Griffith O. H. *Chem. Phys. Lipids*, 1990, 53, 103–113.
10. Gigg, J.; Gigg, R.; Payne, S.; Conant, R. *J. Chem. Soc. Perkin Trans.* I 1987, 1757–1762.
11. Aneja, R.; Aneja, S.; Pathak, V. P.; Ivanova, P. T. *Tetrahedron Lett.* 1994, 35, 6061–6062.
12. Gou, D. M.; Liu, Y. K.; Chen, S. C. *Carbohydr. Res.* 1992, 234, 51–64.
13. Chouinard, P. M.; Bartlett, P. A. *J. Org. Chem.* 1986, 51, 75–78.
14. Aneja R. *Biochem. Soc. Trans.* 1974, 2, 38–41.
15. Aneja, R.; Chadha, J. S.; Davies, A. P. *Biochim. Biophys. Acta*, 1970, 218, 102–111. Aneja, R.; Davies, A. P. *Chem. Phys. Lipids* 1970, 4, 60–71.
16. Freeman, I. P.; Morton, I. D., *J. Chem. Soc.* 1966, 1710–1714. Serdarevich, B. *J. Amer. Oil Chemists' Soc.* 1967, 44, 381–385.
17. Aneja, R.; Ivanova, P. T. Unpublished.

What is claimed is:

1. Enantiomerically pure 1,2:4,5-di-O-cyclohexylidene-3-O-allyl-myo-inositol.
2. The enantiomerically pure compound of claim 1, wherein said compound is 1D-1,2:4,5-di-O-cyclohexylidene-3-O-allyl-myo-inositol.
3. The enantiomerically pure compound of claim 1, wherein said compound is 1L-1,2:4,5-di-O-cyclohexylidene-3-O-allyl-myo-inositol.
4. The enantiomerically pure compound of claim 1, wherein said compound is prepared by a method comprising esterifying (±)-1,2:4,5-di-O-cyclohexylidene-3-O-allyl-myo-inositol with an optically active carboxylic acid derivative and a tertiary amine; separating the diastereomeric esters by MPLC on silica or by conducting crystallization; and then performing alkali catalyzed hydrolysis of the separated individual esters.
5. The enantiomerically pure compound of claim 4, wherein said optically active carboxylic acid derivative is (1S)-(−)-camphanic acid chloride and wherein said tertiary amine is NEt$_3$.
6. A method for synthesizing D-3 phosphorylated phosphoinositides, comprising the steps of:

(a) preparing the enantiomerically pure starting material:

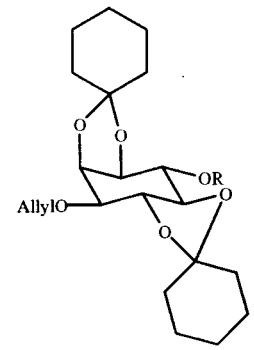

wherein R is H (hydroxyl group), 1D-series;

(b) protecting the hydroxyl group to prepare the 6-O-benzyl derivative:

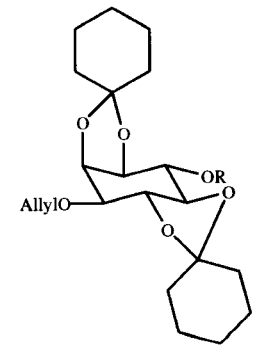

wherein R is benzyl;

(c) selectively removing the 4,5-O-cyclohexylidene protecting group to prepare the 4,5-diol compound:

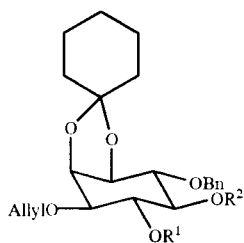

wherein $R^1$ and $R^2$ are H;

(d) protecting the 4- or 5-hydroxyls by partial allylation, or protecting the 4- and 5-hydroxyls by complete allylation, and separating to obtain:

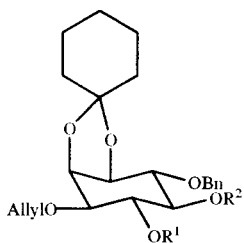

wherein $R^1$ is allyl and $R^2$ is H, or $R^1$ is H and $R^2$ is allyl, and there is one free hydroxyl in each derivative formed by the partial allylation reaction; or wherein both $R^1$ and $R^2$ are allyl and there is no free hydroxyl for the derivative formed by the complete allylation reaction;

(e) further protecting the products of any partial allylation reaction, or the unallylated 4,5-diol derivative, by benzylation of the free hydroxyl to obtain:

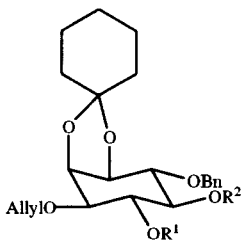

wherein $R^1$ is allyl and $R^2$ is benzyl, or $R^1$ is benzyl and $R^2$ is allyl, or both $R^1$ and $R^2$ are benzyl, and there is no free hydroxyl in any derivative formed;

(f) removing the 1,2-O-cyclohexylidene protecting group from the allylated or benzylated derivatives containing no free hydroxyl to prepare the 1,2-diol compounds:

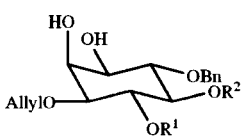

wherein both $R^1$ and $R^2$ are allyl, or $R^1$ is allyl and $R^2$ is benzyl, or $R^1$ is benzyl and $R^2$ is allyl, or both $R^1$ and $R^2$ are benzyl;

(g) selectively protecting the 1-hydroxyl with 4-methoxybenzyl to prepare:

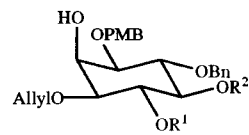

wherein PMB is 4-methoxybenzyl, and both $R^1$ and $R^2$ are allyl, or $R^1$ is allyl and $R^2$ is benzyl, or $R^1$ is benzyl and $R^2$ is allyl, or both $R^1$ and $R^2$ are benzyl;

(h) protecting the free hydroxyl to prepare the 2-benzyl derivatives:

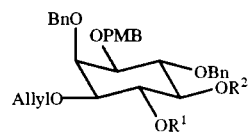

wherein PMB is 4-methoxybenzyl, and both $R^1$ and $R^2$ are allyl, or $R^1$ is allyl and $R^2$ is benzyl, or $R^1$ is benzyl and $R^2$ is allyl, or both $R^1$ and $R^2$ are benzyl;

(i) deprotecting the hydroxyls by removing the allyl group or groups to produce:

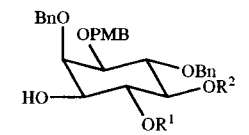

wherein PMB is 4-methoxybenzyl, and both $R^1$ and $R^2$ are H, or $R^1$ is H and $R^2$ is benzyl, or $R^1$ is benzyl and $R^2$ is H, or both $R^1$ and $R^2$ are benzyl;

(j) phosphorylating the deprotected compound to prepare the dibenzylphosphate derivatives:

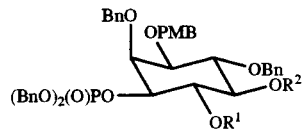

wherein PMB is 4-methoxybenzyl, and both $R^1$ and $R^2$ are dibenzylphosphate, or $R^1$ is dibenzylphosphate and $R^2$ is benzyl, or $R^1$ is benzyl and $R^2$ is dibenzylphosphate, or both $R^1$ and $R^2$ are benzyl;

(k) selectively deprotecting by removing the 4-methoxybenzyl group to produce the 1-hydroxy derivatives:

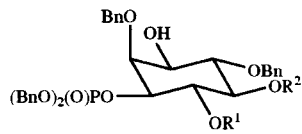

wherein both $R^1$ and $R^2$ are dibenzylphosphate, or $R^1$ is dibenzylphosphate and $R^2$ is benzyl, or $R^1$ is benzyl and $R^2$ is dibenzylphosphate, or both $R^1$ and $R^2$ are benzyl;

(l) condensing the 1-hydroxy derivatives formed by selective deprotection with an sn-3-phosphatidic acid to prepare:

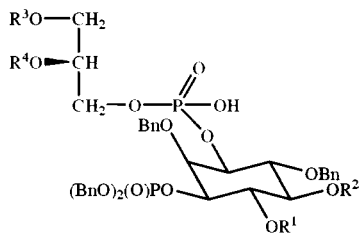

wherein both $R^1$ and $R^2$ are dibenzylphosphate, or $R^1$ is dibenzylphosphate and $R^2$ is benzyl, or $R^1$ is benzyl and $R^2$ is dibenzylphosphate, or both $R^1$ and $R^2$ are benzyl; and wherein $R^3$ and $R^4$ are acyl groups; and (m) completely deprotecting to remove the benzyl ether and benzyl (phosphate)ester groups to prepare the D-3 phosphorylated phosphoinositides:

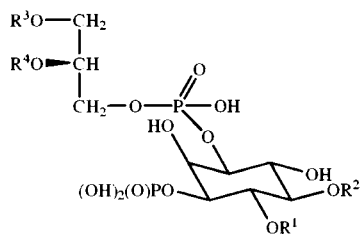

wherein both $R^1$ and $R^2$ are phosphate, or $R^1$ is phosphate and $R^2$ is H, or $R^1$ is H and $R^2$ is phosphate, or both $R^1$ and $R^2$ are H; and wherein $R^3$ and $R^4$ are acyl groups.

7. The method of claim 6, wherein $R^3$ and $R^4$ in the compounds produced by step (l) and step (m) are the same acyl group.

8. The method of claim 6, wherein $R^3$ or $R^4$ in the compounds produced by step (l) and step (m) is a short-chain fattyacyl group.

9. The method of claim 6, wherein $R^3$ or $R^4$ in the compounds produced by step (l) and step (m) is a long-chain fattyacyl group.

10. The method of claim 6, wherein $R^3$ or $R^4$ in the compounds produced by step (l) and step (m) is a hexadecanoyl group.

11. The method of claim 6, wherein $R^3$ or $R^4$ in the compounds produced by step (l) and step (m) is a saturated fattyacyl group.

12. The method of claim 6, wherein $R^3$ or $R^4$ in the compounds produced by step (l) and step (m) is an unsaturated fattyacyl group.

13. The method of claim 6, wherein $R^3$ or $R^4$ in the compounds produced by step (l) and step (m) is a polyunsaturated fattyacyl group.

14. The compound 1D-1-(1',2'-difattyacyl-sn-glycero-3'phospho)-2,6-dibenzyl-myo-inositol-3,4,5-tris(dibenzylphosphate), 1D-1-(1',2'-difattyacyl-sn-glycero-3'-phospho)-2,5,6-tribenzyl-myo-inositol-3,4-bis(dibenzylphosphate), 1D-1-(1',2'-difattyacyl-sn-glycero-3'-phospho)-2,4,6-tribenzyl-myo-inositol-3,5-bis(dibenzylphosphate) or 1D-1-('.2'-difattyacyl-sn-glycero-3'-phospho)-2,4,5,6-tetrabenzyl-myo-inositol-3-dibenzylphosphate, as in the structure:

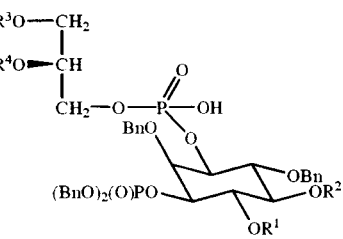

wherein both $R^1$ and $R^2$ are dibenzylphosphate, or $R^1$ is dibenzylphosphate and $R^2$ is benzyl, or $R^1$ is benzyl and $R^2$ is dibenzylphosphate, or both $R^1$ and $R^2$ are benzyl; and $R^3$ and $R^4$ comprise short-chain, long-chain, saturated, unsaturated or polyunsaturated fattyacyl or alkyl residues.

15. The compound of claim 14, wherein said compound is 1D-1-(1',2'-dihexadecanoyl-sn-glycero-3'-phospho)-2,6-dibenzyl-myo-inositol-3,4,5-tris(dibenzylphosphate), 1D-1-(1',2'-dihexadecanoyl-sn-glycero-3'-phospho)-2,5,6-tribenzyl-myo-inositol-3,4-bis(dibenzylphosphate), 1D-1-(1',2'-dihexadecanoyl-sn-glycero-3'-phospho)-2,4,6-tribenzyl-myo-inositol-3,5-bis(dibenzylphosphate) or 1D-1-(1',2'-dihexadecanoyl-sn-glycero-3'-phospho)-2,4,5,6-tetrabenzyl-myo-inositol-3-dibenzylphosphate, as in the structure:

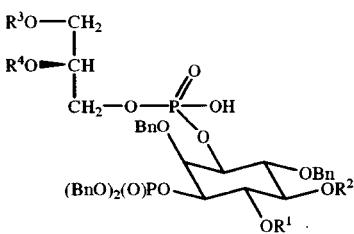

wherein both $R^1$ and $R^2$ are dibenzylphosphate, or $R^1$ is dibenzylphosphate and $R^2$ is benzyl, or $R^1$ is benzyl and $R^2$ is dibenzylphosphate, or both $R^1$ and $R^2$ are benzyl; and $R^3$ and $R^4$ are each hexadecanoyl.

* * * * *